United States Patent [19]
Dirlam et al.

[11] Patent Number: 5,158,937
[45] Date of Patent: Oct. 27, 1992

[54] ACIDIC POLYCYCLIC ETHER ANTIBIOTIC HAVING ANTICOCCIDIAL AND GROWTH PROMOTANT ACTIVITY

[75] Inventors: John P. Dirlam, Gales Ferry; Walter P. Cullen, East Lyme, both of Conn.; Hiroshi Maeda; Junsuke Tone, both of Chita, Japan

[73] Assignee: Pfizer Inc., New York, N.Y.

[21] Appl. No.: 499,484

[22] PCT Filed: Feb. 8, 1988

[86] PCT No.: PCT/US88/00358
§ 371 Date: Jun. 15, 1990
§ 102(e) Date: Jun. 15, 1990

[51] Int. Cl.$^5$ ............ A61K 31/71; C07H 17/04
[52] U.S. Cl. .................. 514/23; 514/25; 536/16.8; 536/18.1
[58] Field of Search ......... 536/16.8, 18.1; 514/27, 514/23, 25; 435/74, 825

[56] References Cited

U.S. PATENT DOCUMENTS

| | | | |
|---|---|---|---|
| 4,148,882 | 4/1979 | Celmer et al. | 424/122 |
| 4,195,079 | 3/1980 | Celmer et al. | 424/122 |
| 4,582,822 | 4/1986 | Hamill et al. | 536/16.3 |
| 4,992,423 | 2/1991 | Cullen et al. | 514/27 |

FOREIGN PATENT DOCUMENTS 341019  2/1989  European Pat. Off. .

OTHER PUBLICATIONS

Current Chemotherapy and Infectious Disease, Proc. 11th ICC and 19th ICAAC, Am. Soc. Microbiol., 1980, pp. 469–470.
Kusakabe et al., J. Antibiotics (Japan), v. 60, pp. 237–238 (1987).
Chemical Abstracts 104:166918w (abstracting EP 169,011).

*Primary Examiner*—Johnnie R. Brown
*Assistant Examiner*—Elli Peselev
*Attorney, Agent, or Firm*—Peter C. Richardson; J. Trevor Lumb; D. Stuart McFarlin

[57] ABSTRACT

An acidic polycyclic ether antibiotic, having structure established by X-ray crystallography, is formed by fermentation of a novel microorganism, *Actinomadura* sp. ATCC 53708. This novel antibiotic is useful as an anticoccidial in chickens, in the prevention or treatment of swine dysentery, and as a growth promotant in cattle and swine.

6 Claims, No Drawings

ACIDIC POLYCYCLIC ETHER ANTIBIOTIC HAVING ANTICOCCIDIAL AND GROWTH PROMOTANT ACTIVITY

BACKGROUND OF THE INVENTION

The present invention concerns a new acidic polycyclic ether antibiotic having the formula:

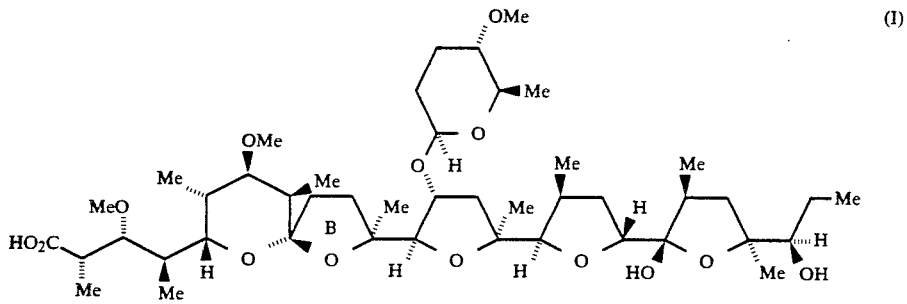

wherein Me=CH$_3$, having absolute stereochemistry as shown; pharmaceutically acceptable cationic salts thereof; nutrient feed compositions comprising said antibiotic for poultry, cattle or swine; its use as an anticoccidial agent in poultry, in the treatment or prevention of swine dysentery, or as a growth promotant in cattle or swine; a fermentation method for its preparation; and the Actinomadura sp. microorganism which produces said antibiotic in said fermentation method.

The compound (I) is a new member of the acidic polycyclic ether group of antibiotics. This family includes such well known agents as monensin (The Merck Index, 10th Ed., Merck and Co.,Inc., Rahway, N.J., 1983, monograph no. 6100), nigericin (loc. cit., monograph no. 6390), narasin (loc. cit., monograph no. 6271), lasalocid (loc. cit., monograph no. 5204), and salinomycin (loc. cit., monograph no. 8193). The subject has been reviewed by Westley, "Polyether Antibiotics", Adv. Appl. Microbiol., vol. 22, pp. 77-223 (1977). Most closely related structurally to the present compound is portmicin, an antibiotic independently reported by Hamill et al , U.S. Pat. No. 4,582,822 and by Kusakabe et al., European patent application 158,179; Tetrahedron Letters, vol. 28, pp. 3357-3360(1987); J. Antibiotics, vol. 40, pp. 237-238(1987). The latter compound possesses an alpha-hydrogen on the tetrahydrofuran B-ring where the present compound possesses an alpha-methyl group. These compounds are generally known as coccidiostats, as feed additive-growth promotants, and/or as agents useful against swine dysentery.

SUMMARY OF THE INVENTION

A culture of Actinomadura sp., ATCC 53708, when fermented under aerobic conditions in aqueous media, produces a new acidic polycyclic ether antibiotic, a compound having the formula (I), as specified above.

The present invention is directed to said compound of the formula (I), including the pharmaceutically-acceptable cationic salts thereof, and to a process for its preparation which comprises fermentation of said Actinomadura sp. ATCC 53708 in an aqueous nutrient medium comprising an assimilable source of carbon and nitrogen until a recoverable amount of said compound of the formula (I) is formed, preferably under submerged aerobic conditions For use as an anticoccidial agent, in the prevention or treatment of swine dysentery, and/or as a growth promotant, the compound (I) is not necessarily separated from the fermentation and isolated in substantially pure form, but is alternatively used in crude form, either in precipitated form admixed with mycelium (recovered by filtration of the fermentation medium), or in solids obtained by spray- or freeze-drying the entire fermentation medium.

Said pharmaceutically-acceptable cationic salts include, but are not limited to, those of sodium, potassium, calcium, ammonia, N,N'-dibenzylethylenediamine, N-methylglucamine (meglumine) and diethanolamine. The preferred cationic salts are those of potassium and sodium.

The present invention is also directed to nutrient feed compositions, one for cattle or swine which comprises the compound of the formula (I) in an amount effective to promote growth and/or improve the feed utilization of said cattle or swine, or to prevent or treat dysentery in swine; and the other for poultry which comprises the compound of the formula (I) in an amount effective to control coccidial infection in said poultry.

The present invention is further directed to a method for promoting growth and/or increasing the efficiency of feed utilization in swine or cattle which comprises administering to said swine or cattle a growth promoting or feed-utilization efficiency promoting amount of the compound of the formula (I), particularly in the form of a nutrient feed composition; to a method for preventing or treating dysentery in swine which comprises administering to said swine a compound of the formula (I) in an amount effective in preventing or treating said dysentery in said swine; and to a method for controlling coccidial infections in poultry which comprises administering to said poultry an anticoccidially effective amount of the compound of the formula (I), particularly in the form of a nutrient feed composition.

Finally, the present invention is directed to a biologically pure culture of Actinomadura sp. ATCC 53708, said culture being capable of producing the compound of the formula (I) in a recoverable quantity upon fermentation in an aqueous nutrient medium comprising assimilable sources of carbon and nitrogen; including said culture in freeze-dried form.

DETAILED DESCRIPTION OF THE INVENTION

The culture capable of producing the present polycyclic ether antibiotic of the formula (I) is designated Actinomadura sp., and has been deposited in The American Type Culture Collection, Rockville, Md. as the type culture under their accession number ATCC 53708. Permanency of the deposit of this culture at The American Type Culture Collection at Rockville, Md.

and ready accessibility thereto by the public are afforded throughout the effective life of the patent in the event the patent is granted. Access to the culture is available during pendency of the application under 37 CFR 1.14 and 35 USC 122. All restrictions on the availability to the public of the culture deposited will be irrevocably removed upon granting of the patent.

This novel culture was derived from a soil sample collected in Tuzla, Istanbul, Turkey, and identified in the culture collection of Pfizer Inc. as N777-1. Its description and classification were provided by Dr. L. H. Huang. This culture was found to produce narrow dimensions of the hyphae of the actinomycetes, an aerial mycelium upon which short spore chains are produced, and an unfragmented substrate mycelium. The results of the whole cell analyses further indicate that it belongs to the genus Actinomadura.

A slant culture of the microorganism was planted into ATCC 172 broth and grown for four days at 28° C. on a shaker. It was then centrifuged for 20 minutes, washed three times with sterile distilled water, and planted on media commonly used for identification of members of the Actinomycetales.

The cultures were incubated at 28° C. and the results read at varying times, but most commonly at fourteen days. The colors were described in common terminology, but exact colors were determined by comparisons with color chips from *The Color Harmony Manual*, fourth edition. The methods of whole-cell amino acid and sugar analyses are those described in Becker et al., Appl. Microbiol., vol. 12, pp. 421-423 (1964), and in Staneck et al., Appl Microbiol., vol. 28, pp. 226-231 (1974) and Lechevalier, J. Lab. Clin. Med., Vol 71, pp. 934-944 (1968), respectively.

The culture was identified as follows:

Yeast Extract-Malt Extract Agar (ISP #2 medium, Difco)—Growth good, cream (2 ca) with dark gray to black (near gray series 5 ih, 5 ml) dots, raised, wrinkled; aerial mycelium none to sparse, colorless; reverse cream to pale yellowish (2 ca, 2 ea) with black (near gray series 5 ml) dots; no soluble pigment.

Oatmeal Agar (ISP #3 medium, Difco)—Growth moderate, cream (2 ca), slightly raised, smooth; aerial mycelium none to sparse, colorless; reverse cream (2 ca); soluble pigment cream (2 ca).

Inorganic Salts-Starch Agar (ISP #4 medium, Difco)—Growth poor, cream (2 ca), thin, smooth; aerial mycelium none to sparse, colorless; reverse cream (2 ca); no soluble pigment.

Glycerol-Asparagine Agar (ISP #5 medium, Difco)—Growth poor to moderate, cream (2 ca), thin, smooth, no aerial mycelium; reverse cream (2 ca); no soluble pigment.

Czapek-Sucrose Agar (Waksman, "The Actinomycetes", v. 2, medium #1, p. 328, 1961)—Growth moderate to good, cream (2 ca), moderately raised, smooth, no aerial mycelium; reverse cream (2 ca); no soluble pigment.

Glucose-Asparagine Agar (ibid., medium #2)— Growth moderate, cream (2 ca), thin to moderately raised, smooth to wrinkled, no aerial mycelium; reverse cream (2 ca); no soluble pigment.

Gordon and Smith's Tyrosine Agar (Gordon and Smith, J. Bacteriol., 69:147-150, 1955)—Growth moderate to good, cream (2 ca), slightly to moderately raised, smooth to wrinkled, no aerial mycelium; reverse cream (2 ca); soluble pigment pale yellowish (2 ea).

Calcium Malate Agar (Waksman, Bacteriol. Rev. 21, 1-29, 1957)—Growth scant, cream (2 ca), thin, smooth; no aerial mycelium, reverse cream (2 ca), no soluble pigment.

Casein Agar (Gordon and Smith, ibid.)—Growth good, cream (2 ca), raised, smooth to wrinkled, no aerial mycelium; reverse pale yellowish (2 ea); with yellowish (2 ga) soluble pigment.

Bennett's Agar (Waksman, loc. cit., medium #30, p. 331)—Growth good, cream (2 ca), raised, wrinkled, no aerial mycelium; reverse cream to pale yellowish (2 ca, 2 ea); soluble pigment pale yellowish (2 ea).

Emerson's Agar (ibid., medium #28, p. 331)— Growth moderate, cream to pale yellowish (2 ca, 2 ea), raised, wrinkled, no aerial mycelium; reverse yellowish (2 ic); no soluble pigment.

Nutrient Agar (ibid., medium #14, p. 330)—Growth poor to moderate, cream (2 ca), thin to slightly raised, no aerial mycelium; reverse cream (2 ca); no soluble pigment.

Gelatin Agar (Gordon and Mihm, J. Bacteriol. 73, 15-27, 1957)—Growth good, cream (2 ca), raised, wrinkled, no aerial mycelium; reverse cream to pale yellowish (2 ca, 2 ea); soluble pigment page yellowish (2 ea).

Starch Agar (ibid )—Growth good, cream (2 ca), raised, wrinkled, no aerial mycelium; reverse cream to pale yellowish (2 ca, 2 ea); no soluble pigment.

Potato Carrot Agar (Lechevalier, Lab. Clin. Med., 71, 934-944, 1968, but use only 30 g. potatoes, 2.5 g. carrots and 20 g. agar)—Growth poor to moderate, off-white (near gray series 2 ba), thin, smooth; aerial mycelium none to sparse, colorless; reverse colorless to cream (2 ca); no soluble pigment.

Tap Water Agar (2%)—Growth poor, cream (2 ca), thin, smooth; aerial mycelium none to sparse, colorless; reverse colorless to cream (2 ca); no soluble pigment.

Gauze's Mineral Medium 1 (Gauze et al., Problems in the Classification of Antagonistic Actinomycetes, English Ed., p. 13, 1957)—Growth poor to moderate, cream (2 ca), thin, smooth; aerial mycelium none to sparse, colorless; reverse cream (2 ca); no soluble pigment.

Gauze's Organic Medium 2 (ibid.)—Growth good, cream (2 ca), raised, wrinkled, no aerial mycelium; reverse cream to pale yellowish (2 ca, 2 ea); no soluble pigment.

Morphological Properties—The morphological properties were observed after three weeks of incubation on inorganic salts-starch agar: aerial mycelium colorless, white to cream; spore chains straight, curved, or hooked, two to nine spores per spore chain; spores globose, oval to elliptical, 0.8-1.4 micron diameter or 1.1-1.8×0.8-1.2 microns; smooth, as revealed by scanning electron microscopy.

Biochemical Properties—Melanin not produced; hydrogen sulfide not produced; gelatin liquefied; starch not hydrolyzed; nitrate not reduced to nitrite; no growth and no decomposition on either Jensen's or Levine and Schoenlein's cellulose broth; no coagulation and no peptonization of milk; casein digestion positive; tyrosine digestion negative; calcium malate digestion negative. Carbohydrate utilization: glucose, arabinose, fructose, mannitol, rhamnose, sucrose, xylose, adonitol, cellobiose, glycerol, maltose, ribose, starch, and trehalose utilized; inositol, raffinose, dulcitol, erythritol, galactose, lactose, mannose, melezitose, melibiose, alpha-methyl-D-glucoside, salicin, sorbitol, and sorbose not utilized.

The other positive tests included utilization of acetate and pyruvate; hydrolysis of esulin; and decomposition of xanthine and hypoxanthine. The following tests were negative: utilization of benzoate, citrate, dextrin, lactate, malate, mucate, oxalate, phenol, propionate and succinate; decomposition of adenine and tyrosine; and hydrolysis of hippurate.

| | Temperature Relations | | |
|---|---|---|---|
| 21° C. | 28° C. | 37° C. | 45° C. |
| Good Growth | Good Growth | Good Growth | Good Growth |

Whole-Cell Analysis—The whole-cell hydrolysates contained meso-diaminopimelic acid, glucose, galactose, madurose, mannose and ribose.

The culture N777-1 is characterized by the cream substrate mycelium; the short, colorless aerial mycelium; the short spore chains which are straight, curved or hooked; and the spores with a smooth surface. It utilized glucose, arabinose, fructose, mannitol, rhamnose, sucrose, xylose, adonitol, cellobiose, glycerol, maltose, ribose, starch, trehalose, acetate, and pyruvate. Xanthine, hypoxanthine, and esculin were decomposed. The whole-cell hydrolysates indicate the presence of mesodiaminopimelic acid and madurose. Thus, the culture N777-1 belongs in the genus Actinomadura, as defined by H. Lechevalier.

The known species of Actinomadura which show similar cream substrate mycelium and/or similar biochemical properties include *A. cremea* subsp. *rifamycini*, *A. madurae* subsp. *simaoensis*, and *A. routienii*. The culture N777-1 differs from *A. cremea* subsp. *rifamycini* in the smooth spores, the failure to reduce nitrate, the failure to utilize raffinose, and the utilization of arabinose and rhamnose.

The culture N777-1 differs from *A. madurae* subsp. *simaoensis* in the cream rather than colorless to orange brown substrate mycelium, the colorless rather than colorless to pink-white aerial mycelium, the failure to reduce nitrate, the failure to decompose tyrosine, and the ability to decompose xanthine. Compared with *A. routienii*, it differs in its absence of pseudosporangia; failure to hydrolyze starch; failure to coagulate milk, and ability to utilize mannitol, fructose, and glycerol.

The culture N777-1 is similar to *A. albolutea* in most of the biochemical tests but differs from the latter in its failure to hydrolyze starch, failure to coagulate milk, cream rather than brown to dark brown substrate mycelium, and short rather than long spore chains.

On the basis of the data presented above, the culture N777-1 is considered as a member of the genus Actinomadura and designated Actinomadura sp. It has been deposited at the American Type Culture Collection under the accession number ATCC 53708.

The antibiotic compuund (I) of the present invention is readily produced by the present Actinomadura sp. by growing at from about 24° to about 36° C. under submerged conditions with agitation and aeration on media consisting of carbohydrate sources such as sugars, starches, glycerol; organic nitrogen substances such as soybean meal, casamino acids, yeast extract; growth substances such as grain solubles, fish meal, cotton seed meal; mineral salts containing trace elements such as iron, cobalt, copper, zinc, etc. and calcium carbonate or phcsphates as buffering agents. After growth has been completed, the antibiotic is readily recovered by extracting the whole broth with an organic solvent such as n-butanol, methylisobutyl ketone, or chloroform at pH ranges from 4.0 to 8.0; by filtering off the mycelium, which contains the precipitated antibiotic, the filtrate being discarded; or by simply spray-drying or freeze-drying the whole broth. Alternatively, the mycelium or the whole dried broth is extracted with one of said organic solvents. The purified antibiotic compound, if that is desired, is isolated from the organic extract by standard methods of concentration, salt or free acid formation, chromatography, precipitation and/or crystallization, as exemplified below.

In the usual manner of carrying out the fermentation, an inoculum is first prepared by scraping vegetative cells, growing on a suitable media, from slants or Roux bottles which have been inoculated with Actinomadura sp. ATCC 53708. The resulting vegetative cells are in turn used to inoculate shake flasks or inoculum tanks, also containing suitable growth media. Alternatively, the inoculum tanks are inoculated from the shake flasks. Following a suitable growth period (generally 120 to 144 hours in shake flasks and 168 to 196 hours in inoculum tanks), a fermenter, also containing suitable growth media, is inoculated under aseptic conditions with vegetative broth from the shake flasks or inoculum tanks. Upon completion of growth (generally about 120–196 hours), the antibiotic compound is recovered in crude or pure form, as desired, by one or another of the methods generally described above, or by specific methods which are exemplified below.

The compound of the formula (I) is tested for in vitro antibacterial activity by standard methods in which the minimum inhibitory concentrations (MIC's) in mcg/ml against one or more microorganisms is measured. One such procedure is the one recommended by the International Collaborative Study on Antibiotic Sensitivity Testing (Ericcson and Sherris, *Acta. Pathologica et Microbiologia Scandinav*, Supp. 217, Section B: 64–68 [1971]), and employs brain heart infusion (BHI) agar and an inocula replicating device. Overnight growth tubes are diluted 100 fold for use as the standard inoculum (20,000–100,000 cells in approximately 0.002 ml. are placed on the agar surface; 20 ml. of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye. Like other polycyclic ether antibiotics, the present compound of the formula (I) typically shows Gram positive antibacterial activity, as well as activity against *Treponema hyodysenteriae*, (the causative agent of swine dysentery) as illustrated in Table (I).

TABLE I

| IN VITRO ANTIBACTERIAL ACTIVITY OF THE COMPOUND OF THE FORMULA (I) | | |
|---|---|---|
| Organism | Strain No. | MIC, mcg/ml |
| *Clostridium perfringens* | 10A006 | 0.39 |
| | 10A009 | 0.20 |
| *Actinomyces pyogenes* | 14D002 | 0.39 |
| | 14D008 | 0.39 |
| | 14D011 | 0.39 |
| *Treponema hyodysenteriae* | 94A001 | 0.20 |
| | 94A002 | 0.20 |
| | 94A007 | 0.20 |

Efficacy data for the compound of the formula (I) and its salts against coccidial infections in chickens is obtained by the following method. Groups of 3-5 ten-day old pathogen free white leghorn cockerel chicks are fed a mash diet containing the compound (I) or its sodium and/or potassium salt uniformly dispersed therein. After being on this ration for 24 hours each chick is inoculated per os with oocysts of the particular species of Eimeria being tested. Other groups of 3-5 ten-day old chicks are fed a similar mash diet without compound (I) or its salts. They are also infected after 24 hours and serve as infected controls. Yet another group of 3-5 ten-day old chicks are fed the same mash diet without antibiotic and are not infected with coccidia. These served as normal controls. The results of treatment are evaluated after five days in the case of *E. acervulina*, and six days for all other challenges.

The criteria used to measure anticoccidial activity consists of lesion scores of 0 to 4 for *E. tenella* after J. E. Lynch, "A New Method of the Primary Evaluation of Anticoccidial Activity", Am. J. Vet. Res., 22, 324-326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks", Exp. Parasit., 28, 30-36, 1970. Activity is measured by dividing the lesion score of each treated group by the lesion score of the infected control. In this test, the compound (I) and its cationic salts exhibit excellent activity against *Eimeria tenella, E. acervulina, E. maxima, E. brunetti* and *E. necatrix* infections in poultry when incorporated into the mash diet of chickens at levels of about 1.0 to 25 ppm. For example, against a sensitive *E. tenella*, the compound of the formula (I) showed 100% control of lesions at doses as low as 5 ppm.

The present compound of the formula (I) is also generally useful in combination with certain other known anticoccidial agents, such as nicarbazin, 4,4'-dinitrocarbanilide or a naphthalenamine, as defined by Hamill et al., U.S. Pat. No. 4,582,822, cited above.

For the prevention or control of coccidiosis in poultry, the compound of this invention is orally administered to poultry in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid concentrate, or added directly to the feed as such, or in the form of a premix or concentrate. A premix or concentrate of therapeutic agent in a carrier is commonly employed for the inclusion of the agent in the feed. The therapeutic agent can be in substantially pure form (e.g., the free acid, or a pharmaceutically-acceptable salt thereof), in assayed crude form such as wet or dry mycelium or dried whole broth. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates are blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements are added directly to the poultry feed to product a nutritionally balanced, finished feed containing a therapeutically effective level of one or more of the compounds of this invention. The mixtures are thoroughly blended by standard procedures, such as in a twin shell blender, to ensure homogeneity.

For use in poultry, the use levels of the compound described herein will vary under different circumstances. Continuous low-level medication, during the growing period; that is, during the first 5 to 12 weeks for chickens, is an effective prophylatic measure. In the treatment of established infections, higher levels may be necessary to overcome the infection. The use level of the compound (I) in feed will generally be in the range of about 1.0 to 25 ppm, preferably in the range of about 2.5 to 12.5 ppm. When administered in drinking water, the level which will be that which will provide the same daily dose of medication factored by the weight ratio of the average daily consumption of feed to the average daily consumption of water.

The activity of the compound of the formula (I) and its salts in promotion growth and/or increasing the efficiency of food utilization in swine or cattle can be measured directly by feeding test groups of animals various levels of the compound (I) or a salt in feed. Alternatively, British Patent Specification No. 1,197,826 details an in vitro rumen method for the evaluation of antibiotics in feeds.

For use in the prevention or treatment of swine dysentery, or in promoting growth and/or increasing the efficiency of feed utilization in cattle or swine the compound of the formula (I) or a salt is preferably administered as a feed additive. The feeds prepared according to methods fully analogous to those detailed above for the preparation of poultry feed, with the same concern for producing feeds in which the therapeutic agent is uniformly dispersed. The use level of the compound (I) in cattle or swine feed will generally be in the range of about 0.25 to 25 ppm. In ruminants the compound of the formula (I) can also be orally administered in the form of a bolus which is retained in the rumenoreticular sac, releasing the therapeutic agent at a substantially constant rate over a prolonged period of time, e.g., 4-8 weeks, providing a dose equivalent to that of the above daily dose in feed, i.e.:

$$\frac{\text{average daily dose}}{\text{in milligrams}} = \frac{(0.25 \text{ to } 25)}{\text{ppm}} \times \frac{\text{average daily feed}}{\text{consumption in Kg}}.$$

Exemplary of such a controlled release bolus is that of Cardinal, U.S. Pat. No. 4,601,893.

The present invention is illustrated by the following examples. However, it should be understood that the invention is not limited to the specific details of these examples.

EXAMPLE 1

Fermentation of Actinomadura sp. ATCC 53708

Isolation of the compound (I) as the Sodium Salt

The Actinomadrua sp. was initially grown by inoculating solid media on slants or Roux bottles with the ATCC 53708 culture, using ATCC medium No. 172, prepared and having composition as follows.

|  | Grams/liter |
|---|---|
| Glucose | 10 |
| Soluble Starch | 20 |
| Yeast Extract | 5 |
| Casein Enzymatic Hydrolysate | 1 |
| Calcium Carbonate | 1 |
| Distilled Water to 1000 ml; pH to 7.0 with KOH; Add Agar | 20 |

Meanwhile, shake flasks were prepared using one or the other of the following media:

| C' | Grams/liter | JDYTT | Grams/liter |
|---|---|---|---|
| Cerelose | 10 | Cerelose | 10 |
| Soy Flour | 10 | Corn Starch | 5 |
| Corn Fermentation Solids | 5 | Corn Steep Liquor | 5 |
| Corn Starch | 10 | Casein Enzymatic Hydrolysate | 5 |
| Sodium Chloride | 5 | Cobalt Chloride | 0.002 |
| Cobalt Chloride | 0.002 | Calcium Carbonate | 3 |
| Calcium Carbonate | 1 | | |

One hundred ml of medium was distributed into 300 ml shake flasks and sterilized at 120° C. and 15 p.s.i. for 30 minutes. After cooling, the medium was inoculated with a vegetative cell suspension scraped from the above Actinomadura sp. slant culture. The flasks were shaken at 28° C. on a shaker having a displacement of 1.5 to 2.5 inches and 150 to 200 cycles per minute (CPM) for five to seven days.

Meanwhile, 5 liter fermentation vessels were prepared containing 3 liters of one of the above C' or JDYTT media or the following media:

| UK1-2 | Grams/liter |
|---|---|
| Cerelose | 45 |
| Soy Flour | 10 |
| Corn Steep Liquor | 10 |
| Cobalt Chloride | 0.002 |
| Magnesium Sulfate | 0.10 |
| Calcium Carbonate | 3 |
| Manganese Sulfate | 0.10 |
| Ferric Sulfate | 0.10 |

An antifoaming agent (polypropyleneglycol, P2000, containing 10% ethylene oxide by weight, 1 ml) was added, and the vessels were sealed and sterilized at 120° C. and 15 p.s.i. for 45 minutes. The vessels were then inoculated with one shake flask (ca 3% inoculum), fermented for 120 to 168 hours at 30° C., stirring at 1700 revolutions per minute (RPM) with an air rate of one volume of air per volume of liquid per minute.

When the fermentation was completed (based on an antibiotic disc assay versus *B. subtilis* ATCC 6633) the fermenters were stopped and filtered at the natural pH with the aid of a diatomaceous earth. The filter cake was slurried in methanol, concentrated in vacuo, diluted with 2-3 volumes of water then extracted 2× with ⅓ to ½ volume of either methylisobutyl ketone or n-butanol. The solvent layer was separated from the aqueous phase by aspiration or centrifugation, sparkled and concentrated in vacuo to yield the antibiotic of the formula (I) in crude form as a viscous oil.

The bioactivity of the broth and subsequent recovery streams can be followed by using a sensitive strain of *Bacillus subtilis* ATCC 6633 or *Staphylococcus aureus* ATCC 6538. The components in the broth and recovery streams can be visualized by using Analtech silica gel GF plates employing ethyl acetate as eluant. The developed plates are sprayed with vanillin reagent (3 g vanillin in 75 ml ethanol and 25 ml 85% phosphoric acid) and heated to 80° C. The antibiotic product of the formula (I) appears as a purple spot. The developed tlc plate can also be overlayed with agar seeded with either *S. aureus* or *B. subtilis* to which 2,3,5-triphenyl-2H-tetrazolium chloride monohydrate has been added and incubated at 37° C. for 16 hours to visualize the antibiotic (white spots against a pink background).

Scale-up in large fermentation vessels was carried out by preparing shake flasks containing 0.7 liters of C' or JDYTT medium. The shake flask inoculum was fermented for 5 to 7 days at 28° C., and used to inoculate a 200 or a 6000 liter fermentation vessel containing 100 or 4000 liters of UK1-2 medium, respectively. Approximately one liter of inoculum was used in each tank. The fermentations, after proceeding for 7 to 10 days, were harvested.

The whole broth of the smaller fermentation run was extracted with 50 liters of methylisobutyl ketone at natural pH. The organic extract was concentrated under vacuum on a cyclone still and rotary evaporator to an oil. This oil was twice chromatographed on 500 g. of column grade silica gel slurried in hexane. The first column was developed with ethyl acetate and the second with 1:1 $CHCl_3$:acetone. Product containing cuts were identified by tlc using the method described above. The active cuts from the second silica gel column were finally chromatographed on florisil, using $CHCl_3$:$CH_3OH$ 19:1 as eluant. Product cuts were combined, shaken with dilute $H_3PO_4$ and then with dibasic sodium phosphate buffer to form the sodium salt, dried over $Na_2SO_4$, stripped, and the residue crystallized from ether to isolate the sodium salt of the compound of the formula (I), 915 mg; mp 245°-249° C., $[alpha]_D^{25} = -19.0°$ (c=1, $CH_3OH$).

Anal. Calcd. for $C_{45}H_{77}O_{14}Na$: C, 62.47; H, 8.97. Found: C, 62.89; H, 9.22.

C-13 nmr [chemical shift (ppm) in CDCl$_3$ with number of hydrogens in parentheses]: 182.8 (0), 110.0 (0), 106.0 (0), 99.1 (1), 87.2 (1), 86.9 (0), 86.2 (1), 86.2 (0), 84.8 (1), 83.4 (0), 82.6 (1), 80.2 (1), 78.5 (1), 75.2 (1), 74.8 (1), 74.6 (1), 66.4 (1), 60.3 (3), 57.9 (3), 56.9 (3), 44.5 (1), 39.0 (1), 36.9 (1), 36.8 (2), 35.9 (2), 35.4 (2), 35.2 (2), 35.1 (1), 35.0 (1), 31.3 (2), 30.9 (2), 30.5 (1), 28.2 (3), 27.1 (2), 26.1 (2), 25.0 (3), 21.0 (3), 18.3 (3), 16.7 (3), 15.3 (3), 13.4 (3), 13.1 (3), 11.2 (3), 10.7 (3), and 10.6 (3).

Work up of the large tank fermentation of whole broth was carried out by extracting the approximately 4000 liters of whole broth with 1800 liters of methylisobutyl ketone, separating the solvent on a Podbielnack extractor and concentrating the solvent to a thin syrup in vacuo. The concentrate was triturated 2 times with an equal volume of neat methanol, separated from the methanol insoluble oil, and the methanol triturate concentrated in vacuo to a syrup. The latter was extracted 2× with hexane and the combined hexane extracted with acetonitrile. The acetonitrile was retained for future recovery. The hexane was then concentrated in vacuo, then batch chromatographed on silica gel. The silica gel was desorbed on a filter funnel first with hexane, then methylene chloride, ethyl acetate and finally with acetone. The active cuts, which were in the CH$_2$Cl$_2$ and ethyl acetate eluates, were concentrated, dissolved in hexane and washed with acid water, then extracted with 1% N-methyl-D-glucamine in water. The aqueous phase was salted with sodium chloride and extracted 2× with an equal volume of ethyl acetate. The organic layers were combined, treated with activated carbon, filtered, washed with pH 9.0 sodium phosphate buffer, dried over sodium sulfate, concentrated in vacuo and crystallized from ether to yield 50.8 g. of sodium salt identical with the product of the smaller scale fermentation.

EXAMPLE 2

Compound (I) in the Free Acid Form

The free acid form of the antibiotic of the formula (I) was prepared by vigorously shaking a chloroform solution of the sodium salt with an equal volume of hydrochloric acid at pH 2 in a separatory funnel. The phases were separated, and the chloroform layer was washed with water and then evaporated under vacuum to give the free acid: mp 87°–90° C.; [alpha]$_D^{25}$ = −6.9° (c = 1, methanol).

Anal. Calcd for C$_{45}$H$_{78}$O$_{14}$·0.5H$_2$O: C, 63.43; H, 9.34. Found: C, 63.35; H, 9.53.

EXAMPLE 3

The Sodium Salt of the Compound (I)

The free acid of the preceding Example (45 mg) was dissolved in 100 ml of chloroform. A solution of sodium carbonate (0.5 g) in water (100 ml) was added and the resulting mixture was then placed in a separatory funnel and vigorously shaken for several minutes. The chloroform layer was separated and the aqueous layer was washed with fresh chloroform. The combined chloroform extracts were dried over sodium sulfate, filtered, and evaporated to afford 41 mg of the sodium salt; mp 230°–235° C.

Anal. Calcd for C$_{45}$H$_{77}$O$_{14}$Na: C, 62.47; H, 8.97. Found: C, 62.20; H, 9.14.

EXAMPLE 4

The Rubidium Salt of the Compound (I)

To prepare the rubidium salt of the compound of the formula (I), the free acid (30 mg) was dissolved in 50 ml of chloroform. Rubidium carbonate (35 mg in 25 ml of water) was added to the chloroform and the mixture was allowed to stir for 2 hours. The organic phase was separated and the aqueous layer was extracted with an equal volume of chloroform. The combined chloroform extracts were evaporated to afford a white solid. The rubidium salt was recrystallized by slow evaporation from ether and the X-ray structure was determined on the resulting crystals by Dr. J. Bordner.

EXAMPLE 5

The Potassium Salt of the Compound (I)

To prepare the potassium salt of the antibiotic compound of the formula (I), the free acid 130 mg was dissolved in 100 ml of chloroform. K$_2$CO$_3$ (100 mg) in 100 ml of H$_2$O was added and the resulting mixture stirred for several minutes and was then placed in a separatory funnel and vigorously shaken for several minutes. The organic phase was separated and evaporated under vacuum to afford the compound (I) as a white powder; mp 255°–260° C., [alpha]$_D^{25}$ = −19.6° (c = 1, chloroform).

Anal. Calcd. for C$_{45}$H$_{77}$O$_{14}$K: C, 61.34; H, 8.81. Found: C, 60.91; H, 8.83.

We claim:

1. A compound having the formula

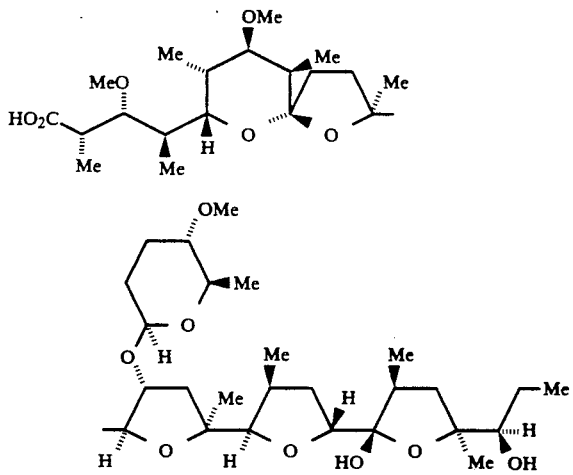

wherein Me represents CH$_3$, or a pharmaceutically acceptable cationic salt thereof.

2. The compound of claim 1 in the form of its sodium or potassium salt.

3. A nutrient feed composition for poultry, cattle or swine which comprises the compound of claim 1 in an amount effective to control coccidial infections in said poultry, in preventing or treating dysentery in said swine, or in promoting growth or improving feed utilization of said cattle or swine.

4. A method for promoting growth or increasing the efficiency of feed utilization in swine or cattle which comprises administering to said swine or cattle a growth promoting or feed-utilization efficiency promoting amount of the compound of claim 1 in the form of a nutrient feed composition.

5. A method for controlling coccidial infections in poultry which comprises administering to said poultry an anticoccidially effective amount of the compound of claim 1.

6. A method of claim 5 wherein the compound is administered to said poultry in the form of a nutrient feed composition.

* * * * *